(12) United States Patent
Fritsch et al.

(10) Patent No.: US 7,175,603 B2
(45) Date of Patent: Feb. 13, 2007

(54) WRIST BRACE

(75) Inventors: John Fritsch, Prairie du Sac, WI (US); Herbert Raschka, Prairie du Sac, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 0 days.

(21) Appl. No.: 10/950,937

(22) Filed: Sep. 27, 2004

(65) Prior Publication Data

US 2006/0069335 A1 Mar. 30, 2006

(51) Int. Cl.
*A61F 5/00* (2006.01)
*A61F 9/00* (2006.01)

(52) U.S. Cl. .................. 602/20; 602/21; 2/16

(58) Field of Classification Search ............ 602/5, 602/20–23, 26–27, 62; 128/878, 879; 2/16, 2/162, 170; 5/646, 647, 623
See application file for complete search history.

(56) References Cited

U.S. PATENT DOCUMENTS

| | | | |
|---|---|---|---|
| 4,182,320 A * | 1/1980 | Sweeney | 602/13 |
| 4,716,892 A | 1/1988 | Brunswick | |
| 4,850,341 A | 7/1989 | Fabry et al. | |
| 4,854,309 A * | 8/1989 | Elsey | 602/21 |
| 4,883,073 A | 11/1989 | Aziz | |
| 5,160,314 A | 11/1992 | Peters | |
| 5,205,812 A | 4/1993 | Wasserman | |
| 5,267,943 A | 12/1993 | Dancyger | |
| 5,307,521 A | 5/1994 | Davis | |
| 5,376,066 A | 12/1994 | Phillips et al. | |
| 5,397,296 A | 3/1995 | Sydor et al. | |
| 5,415,624 A * | 5/1995 | Williams | 602/21 |
| 5,417,645 A | 5/1995 | Lemmen | |
| 5,484,392 A | 1/1996 | Sydor et al. | |
| 5,538,501 A | 7/1996 | Caswell | |
| 5,601,597 A | 2/1997 | Arrowood et al. | |
| 5,695,453 A | 12/1997 | Neal | |
| 5,713,837 A | 2/1998 | Grim et al. | |
| 5,746,707 A | 5/1998 | Eck | |
| 5,759,166 A | 6/1998 | Nelson et al. | |
| 5,766,141 A | 6/1998 | Gould | |
| 5,769,804 A | 6/1998 | Harris et al. | |
| 5,772,620 A | 6/1998 | Szlema et al. | |
| 5,810,753 A | 9/1998 | Eberbach | |
| 5,836,902 A | 11/1998 | Gray | |
| 5,873,130 A | 2/1999 | Lafferty | |
| 5,919,151 A | 7/1999 | Gustafson | |
| 5,925,007 A | 7/1999 | Ashline | |
| 5,983,408 A * | 11/1999 | Li | 2/455 |
| 6,006,751 A | 12/1999 | Spitzer | |
| 6,022,332 A | 2/2000 | Nelson | |
| 6,024,715 A | 2/2000 | Maxwell | |
| 6,056,711 A | 5/2000 | Domanski et al. | |
| 6,093,161 A | 7/2000 | Vlacyen et al. | |

(Continued)

*Primary Examiner*—Teena Mitchell
*Assistant Examiner*—Shumaya Ali
(74) *Attorney, Agent, or Firm*—Rick L. Abegglen

(57) ABSTRACT

A wrist brace is provided for supporting a hand and a wrist of a wearer. The wrist brace includes first and second rigid support members that define a cavity therebetween for receiving at least a portion of the hand and the wrist of a wearer. A removable pillow is operatively connected to the first rigid support member to protect the wrist from possible discomfort due to the impact of the wrist with an external item.

10 Claims, 5 Drawing Sheets

U.S. PATENT DOCUMENTS

| | | |
|---|---|---|
| 6,095,994 A | 8/2000 | Spits |
| 6,102,880 A | 8/2000 | Nelson et al. |
| 6,106,492 A | 8/2000 | Darcey |
| 6,129,692 A | 10/2000 | Mathis |
| 6,142,966 A | 11/2000 | Mathis |
| 6,146,347 A | 11/2000 | Porrata |
| 6,146,348 A | 11/2000 | Slautterback |
| 6,190,344 B1 | 2/2001 | Bobroff |
| 6,199,211 B1 | 3/2001 | Franzolino |
| 6,200,286 B1 | 3/2001 | Zamani |
| 6,213,969 B1 | 4/2001 | MacMorran et al. |
| 6,328,706 B1 | 12/2001 | Yattavong |
| D454,199 S | 3/2002 | Lamping et al. |
| 6,383,157 B1 | 5/2002 | Massi et al. |
| 6,398,748 B1 | 6/2002 | Wilson |
| D461,600 S | 8/2002 | Domanski et al. |
| 6,443,921 B1 | 9/2002 | Kaplan |
| 6,475,174 B1 | 11/2002 | Chow |
| 6,517,501 B1 | 2/2003 | Slautterback |
| 6,517,507 B1 | 2/2003 | Faherty |
| 6,540,705 B2 | 4/2003 | Norstrem et al. |
| 6,540,710 B1 | 4/2003 | Cruz |
| 6,561,994 B1 | 5/2003 | Mills et al. |
| 6,582,382 B2 | 6/2003 | Domanski et al. |
| 6,592,537 B2 | 7/2003 | Stager |
| 6,694,519 B1 | 2/2004 | Stewart |
| 6,716,185 B1 | 4/2004 | Rieger |
| 6,723,061 B2 | 4/2004 | Williams |
| 6,835,182 B2 * | 12/2004 | Darcey .................. 602/20 |
| 2002/0115950 A1 | 8/2002 | Norstrem et al. |
| 2002/0115951 A1 | 8/2002 | Norstrem et al. |
| 2003/0050586 A1 | 3/2003 | Domanski et al. |
| 2003/0083603 A1 | 5/2003 | Nelson |
| 2003/0100855 A1 | 5/2003 | Norstrem |
| 2004/0082894 A1 * | 4/2004 | Stager .................. 602/21 |

\* cited by examiner

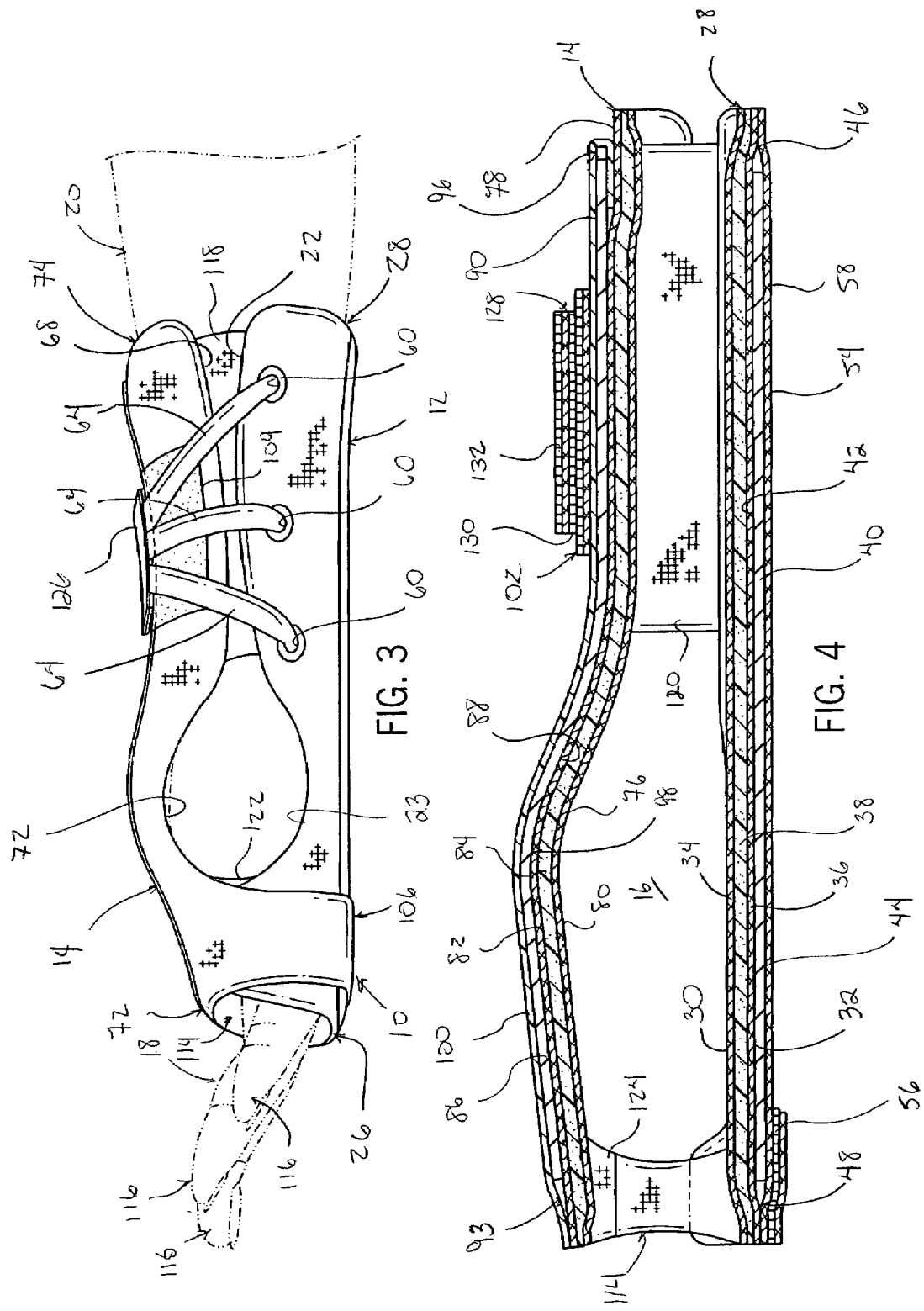

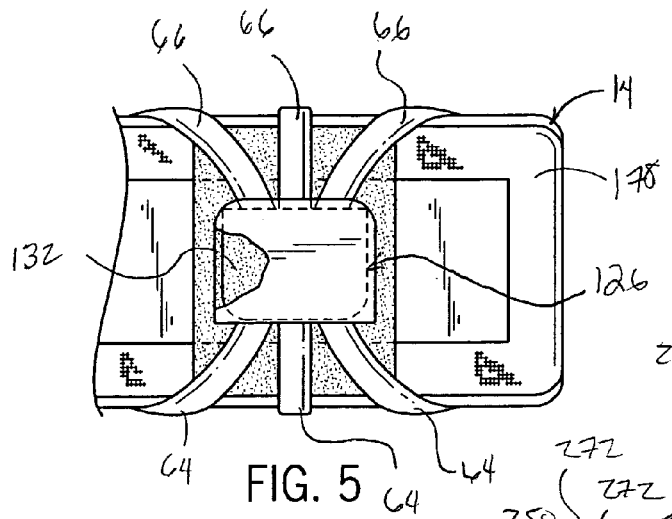
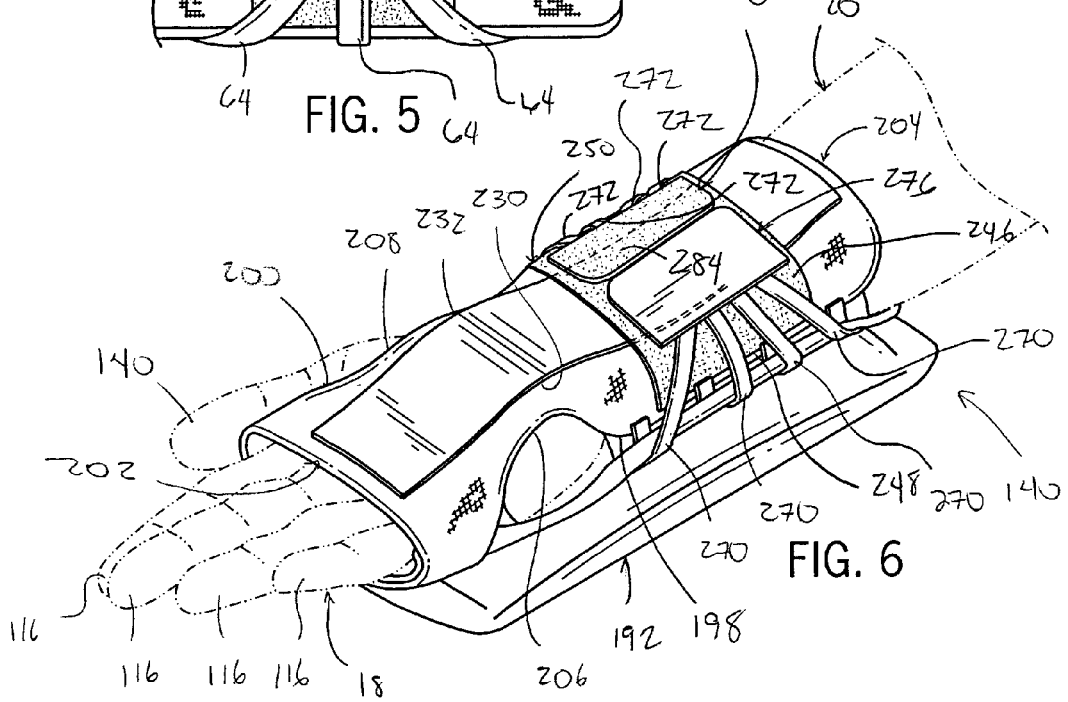
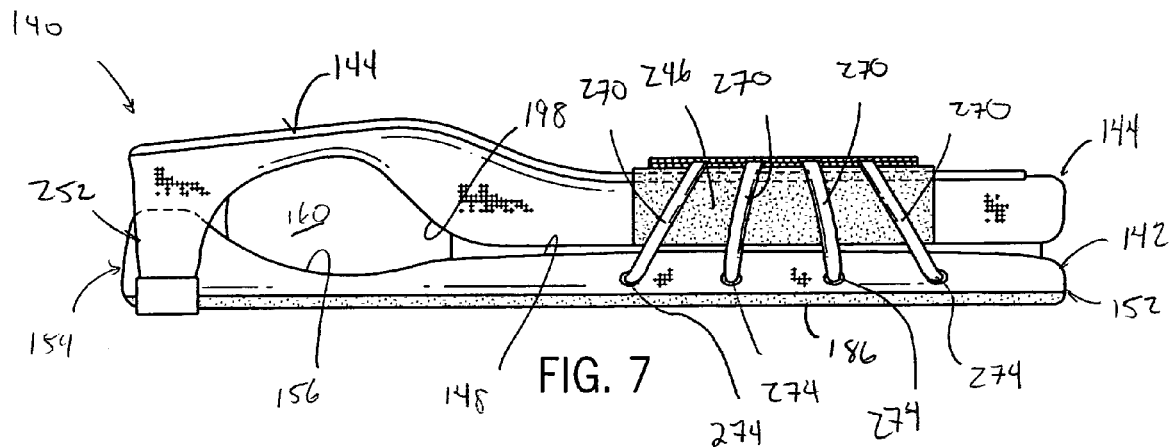

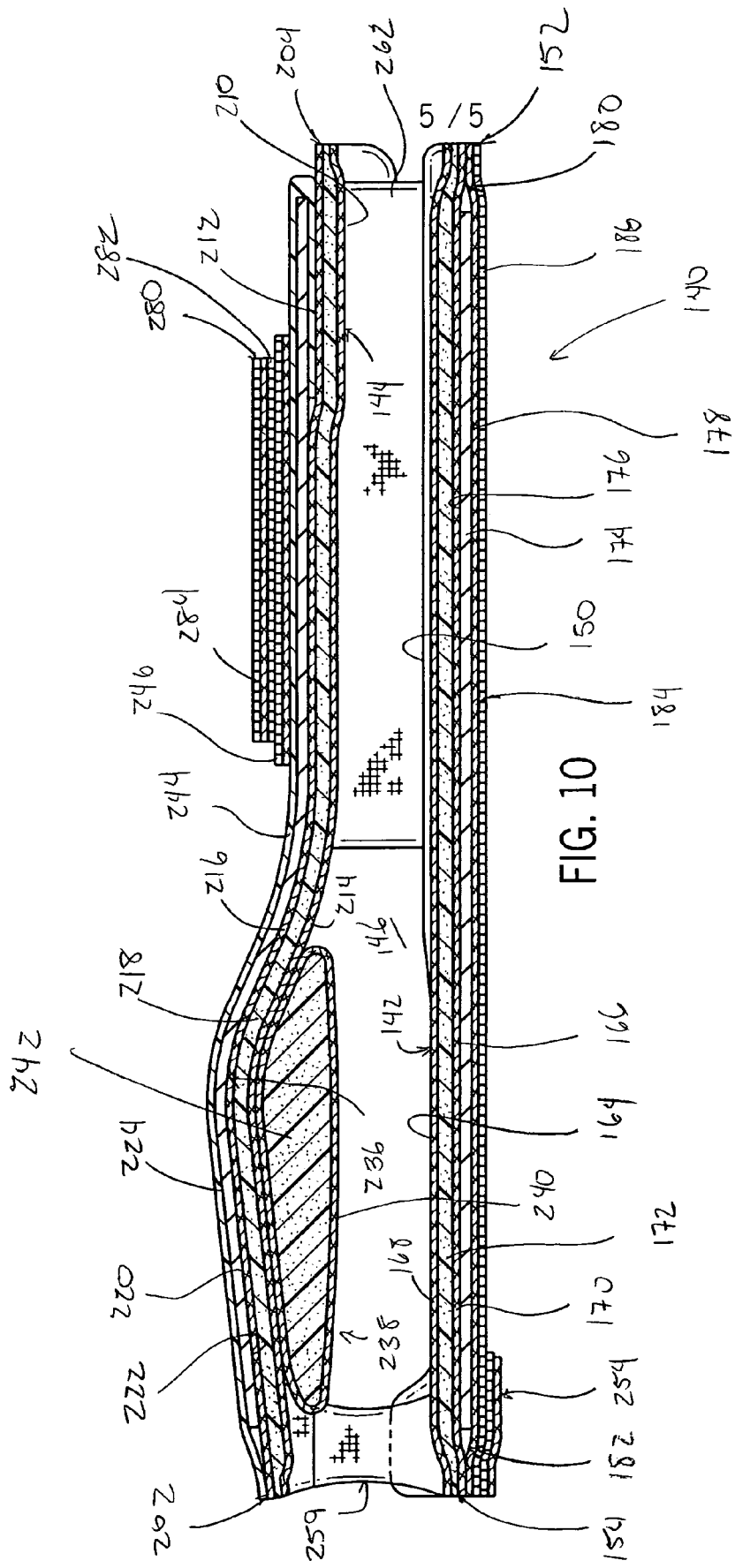

WRIST BRACE

FIELD OF THE INVENTION

This invention relates generally to medical devices, and in particular, to a wrist brace for restricting movement of the wrist of a wearer.

BACKGROUND OF THE INVENTION

Industrial and post-industrial economies have placed emphasis on the efficient performance of specialized tasks. In many fields, this specialization leads to the repetition of similar physical actions dozens or hundreds of times a day. These repeated small tasks can result in injuries which have been grouped together under the heading of Cumulative Repetitive Stress Syndromes (CRSS) or Repetitive Strain Injury (RSI). Particular maladies affecting the wrist include Carpal Tunnel Syndrome and tendonitis. One approach to lessening the pain associated with repetitive wrist movements is to restrain the wrist to prevent the motions which lead to discomfort.

Many wrist braces have been developed to address this need. Some designs are specially configured for the left or the right hand and come in a range of sizes. Where a wrist brace is custom built for a particular patient, the wide range of shapes and sizes is not a concern. However, where the brace is intended for retail sale, providing different braces for left and right wrists demands a doubling of the number of items which must be kept on hand by the retailer. The multiplicity of products, or stock keeping units, is increased proportionately when braces in small, medium, large, or other sizes are also required for each hand. U.S. Pat. No. 5,759,166 to Nelson discloses a wrist brace having a stretchable fabric base which encircles the wrist and is clasped in position by straps and hook and loop fasteners. This unit, although made in various sizes, may be worn on either the left or right hand. A single wrist brace which is suitable for either hand and hands of various sizes, would greatly reduce the inventory required by a particular retailer. In addition, a brace which would perform the necessary motion restricting function with minimal material and minimal discomfort to the wearer would lessen the reluctance of a repetitive strain injury sufferer to make use of the brace.

Further, most prior wrist braces are designed to restrain movement of the wrist in order to prevent pain and discomfort to the wearer. However, these prior wrist braces often provide little or no protection from external impact on the wrist that may also inflict pain on the wearer. The possibility of the wearer inadvertently striking the wrist is especially acute while the wearer is sleeping. It can be appreciated that the wearer may cause further damage and pain to the wrist by inadvertently impacting the wrist during sleep. While wrist braces that provide adequate protection for the wrist of wearer from external impacts are known, these prior wrist braces are often too bulky and unreasonably restrict movement of the wrist by the wearer.

Therefore, it is a primary object and feature of the present invention to provide a wrist brace that may be worn on either hand of an individual and by individuals having wrists of different sizes.

It is a further object and feature of the present invention to provide a wrist brace that provides freedom of motion to the fingers of a wearer.

It is a still further object and feature of the present invention to provide a wrist brace that protects the wrist of a wearer from impact with external items.

It is a still further object and feature of the present invention to provide a wrist brace that is simple to utilize and inexpensive to manufacture.

In accordance with the present invention, a wrist brace is provided for supporting the wrist of an individual. The wrist brace includes a first panel having inner and outer surfaces, a forward end, a rearward end and first and second sides. The wrist brace also includes a second panel having inner and outer surfaces, a forward end, a rearward end, and first and second sides. The inner surface of the second panel and the inner surface of the first panel define a cavity for receiving the wrist of an individual. A first generally flat rigid support is disposed in the first panel and extends between the forward and rearward ends thereof. A second rigid support is disposed in the second panel. The second rigid support extends between the forward and rearward ends of the second panel and has a concave portion extending away from the first panel.

The wrist brace may also include a first rear web interconnected to the first side of the first panel and the first side of the second panel. A first forward web also interconnects the first side of the first panel and the first side of the second panel. The first rear web and the first forward web are axially spaced so as to define a thumb aperture therebetween. Similarly, a second rear web interconnects the second side of the first panel and a second side of the second panel. A second forward web also interconnects the second side of the first panel and the second side of the second panel. The second rear web and the second forward web are axially spaced so as to define a second thumb aperture therebetween.

A connector is provided for adjustably interconnecting the first side of the first panel and the first side of the second panel to vary the size of the cavity. The first panel includes an eyelet extending therethrough adjacent the first side and a connector includes a first end interconnected to the first side of the second panel and a second end having a fastener connectable to the outer surface of the second panel. A hook and pile fastener having a hooked portion and pile portion is also provided. One of the hooked portion and pile portion is interconnected to the outer surface of the second panel and the fastener includes the other of the hooked portion and the pile portion.

A pillow may be removably connected to the outer surfaces of the first panel. A hook and pile fastener interconnects the pillow the outer surface of the first panel. In addition, a second pillow may extend to the inner surface of the second panel adjacent to the forward end to the second panel. First and second connection tabs extend from the second panel. A connection structure removably connects the first and second connection tabs to the first panel.

In accordance with a further aspect of the present invention, a wrist brace is provided for supporting a hand and a wrist of a wearer. The wrist brace includes first and second rigid support members defining a cavity therebetween for receiving at least a portion of the hand and of the wrist of a wearer. A removable pillow is operatively connectable to the first rigid support.

The first rigid support member includes a first flexible panel having an inner surface, outer surface, forward end, rearward end and first and second sides. In addition, the first rigid support member includes a generally flat, first support disposed in the first flexible panel. The first support discourages flexing of the first flexible panel. The second rigid support member includes a second flexible panel having an inner surface, an outer surface, forward end, a rearward end, and first and second sides. A second support is disposed in the second flexible panel. The second support has a concave portion defining a recess for receiving a portion of the hand of the wearer.

A first rear web interconnects the first side of the first panel and the first side of the second panel. A first forward web also interconnects the first side of the first panel and the first side of the second panel. The first rear web and the first forward web are axially spaced so as to define a thumb aperture therebetween.

The wrist brace may also include a second rearward web for interconnecting the second side of the first panel and the second side of the second panel. A second forward web also interconnects the second side of the first panel and the second side of the second panel. The second rear web and the second forward web are axially spaced so as to define a second thumb aperture therebetween.

A connector adjustably interconnects the first side of the first panel and the first side of the second panel to vary the size of the cavity. The first panel includes an eyelet extending therethrough adjacent the first side. The connector extends through the eyelet and includes a first end interconnected to the first side of the second panel and a second end having a fastener connectable to the outer surface of the second panel. The wrist brace also includes hooked and pile fastener having a hooked portion and pile portion. One of the hooked portion and the pile portion is interconnected to the outer surface to the second panel and the fastener includes the other of the hooked portion and the pile portion.

A hook and pile fastener may also be used to interconnect a pillow to the outer surface of the first panel. In addition, a second pillow may be operatively connected to the second panel and extend into the cavity. First and second connection tabs extend from the second panel. A connection structure removably connects the first and second connection tabs to the first panel.

In accordance with a further aspect of the present invention, a wrist brace is provided for supporting a hand and a wrist of a wearer. The wrist brace includes a first flexible panel having an inner surface, an outer surface, a forward end, a rearward end, and first and second sides. A generally flat, first support is disposed in the first flexible panel. The first support discourages the flexing of the first flexible panel. A second flexible panel has an inner surface, an outer surface, a forward end, a rearward end and first and second sides. The second support is disposed on the second flexible panel. The second support has a concave portion defining a recess for receiving a portion of the hand of the wearer. A first rear web interconnects the first side of the first panel and the first side of the second panel. A first forward web also interconnects the first side of the first panel and the first side of the second panel. The first rear web and the first forward web are axially spaced so as to define a thumb aperture therebetween. A second rear web interconnects the second side of the first panel and the second side of the second panel. A second forward web also interconnects the second side of the first panel and the second side of the second panel. The second rear web and the second forward web are axially spaced so as to define a second thumb aperture therebetween. A connector adjustably interconnects the first side of the first panel and the first side of the second panel to vary the size of the cavity.

The first panel includes an eyelet therethrough adjacent the first side. A connector extends through the eyelet and includes a first end interconnected to the first side of the second panel and a second end having a fastener connectable to the outer surface of the second panel. The wrist brace also includes a hook and pile fastener having a hooked and pile portion. One of the hook portion and the pile portion is interconnected to the outer surface of the second panel and the fastener includes the other of the hooked portion and pile portion. The wrist brace may also include a pillow and a hook and pile fastener for removably connecting the pillow to the outer surface of the first panel. A second pillow is operatively connected to the second panel and extends into the cavity. First and second connection tabs extend from the second panel. A connection structure removably connects the first and second connection tabs to the first panel.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 3 is a side elevational view of the wrist brace of the present invention positioned on the wrist of an individual;

FIG. 4 is a cross-sectional view of the wrist brace of the present invention;

FIG. 5 is a top plan view of a portion of the wrist brace of the present invention;

FIG. 6 is a isometric view of a first side of a second embodiment of a wrist brace in accordance with the present invention positioned on the wrist of an individual;

FIG. 7 is a side elevational view of the wrist brace of FIG. 6;

FIG. 10 is a cross-sectional view of the wrist brace of FIG. 6.

DETAILED DESCRIPTION OF THE DRAWINGS

Figure 1:
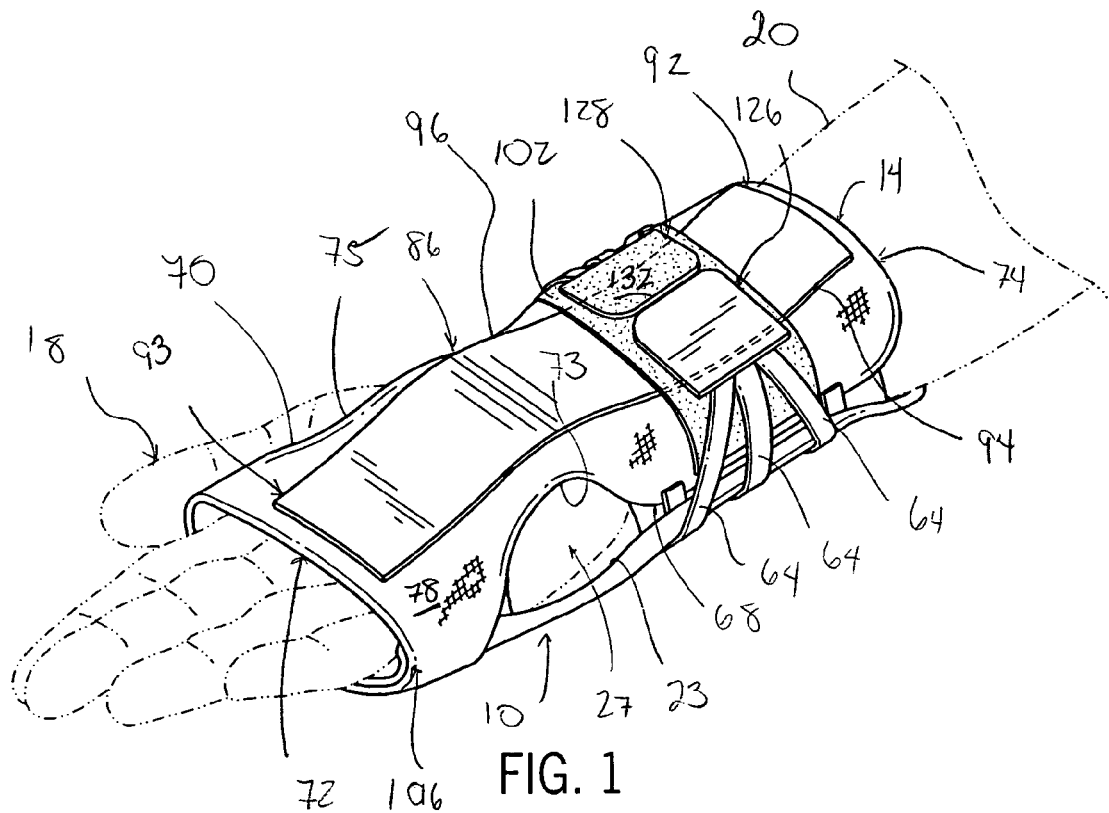
FIG. 1 is an isometric view of a first side of the wrist brace in accordance of the present invention positioned on the wrist of an individual.

Referring to FIGS. 1–5, a first embodiment of a wrist brace in accordance with the present invention is generally designated by the reference numeral 10. Wrist brace 10 includes first and second panels 12 and 14, respectively, that define cavity 16 therebetween for receiving a portion of hand 18 and wrist 20 of a wearer. As hereinafter described, wrist brace 10 is adaptable to be worn on either the left or right wrist of a wearer.

First and second panels 12 and 14, respectively, extend along corresponding axes and are formed from stretchable and breathable materials that allows liquid, such as perspiration, to be drawn away from contact with the skin of a wearer. First panel 12 is defined by first and second sides 22 and 24, respectively, and forward and rearward ends 26 and 28, respectively. First and second sides 22 and 24, respectively, include generally concave, thumb receiving portions 23 and 25, respectively, that partially define thumb apertures 27 and 29, respectively, in wrist brace 10, as hereinafter described. First panel 12 further includes inner surface 30 and outer surface 32. By way of example, first panel 12 may be formed of inner and outer sheets of material 34 and 36, respectively, having absorbent layer 38 captured therebetween.

Wrist brace 10 further includes a generally flat, rigid support 40 having inner surface 42 affixed to outer surface 32 of first panel 12 and an outer surface 44. Support 40 includes rearward end 46 positioned adjacent rearward end 28 of first panel 12 and forward end 48 adjacent forward end 26 of first panel 12. Sides 50 and 52 of support 40 are generally parallel to each other and spaced from corresponding sides 22 and 24, respectively, of first panel 12. Cloth layer 54 overlaps support 40 and is interconnected to outer surface 32 of first panel 12 to secure support 40 in position. Pile pad 56 is mounted to outer surface 58 of cloth layer 54 adjacent forward end 26 of first panel 12, for reasons hereinafter described.

Figure 2:
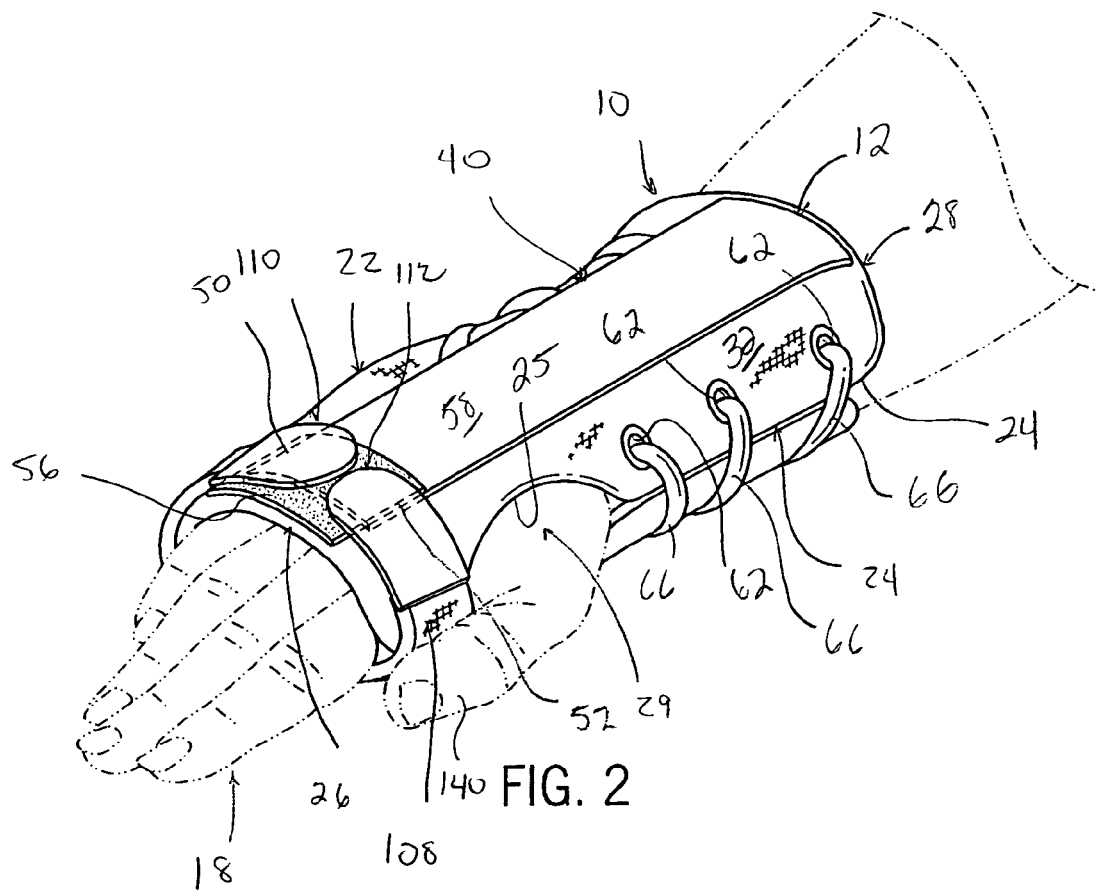
FIG. 2 is an isometric view of a second side of the wrist brace of the present invention positioned on the wrist of an individual.
Figure 8:
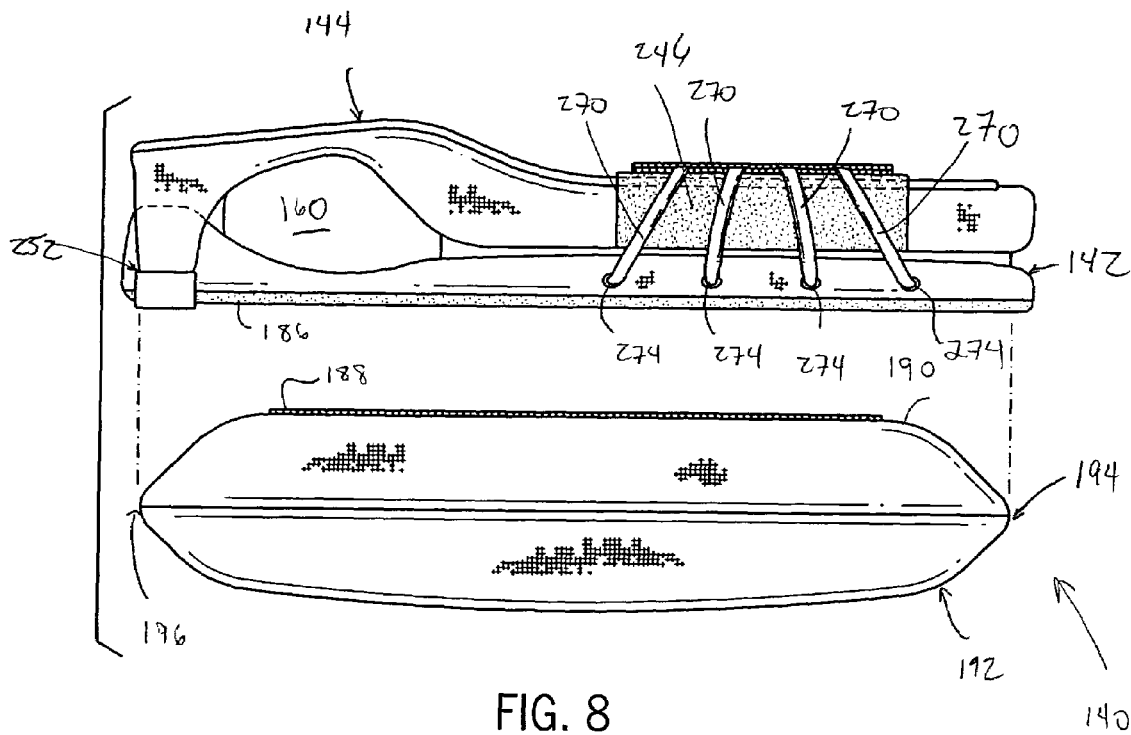
FIG. 8 is an exploded, side elevational of the wrist brace of FIG. 6.
Figure 9:
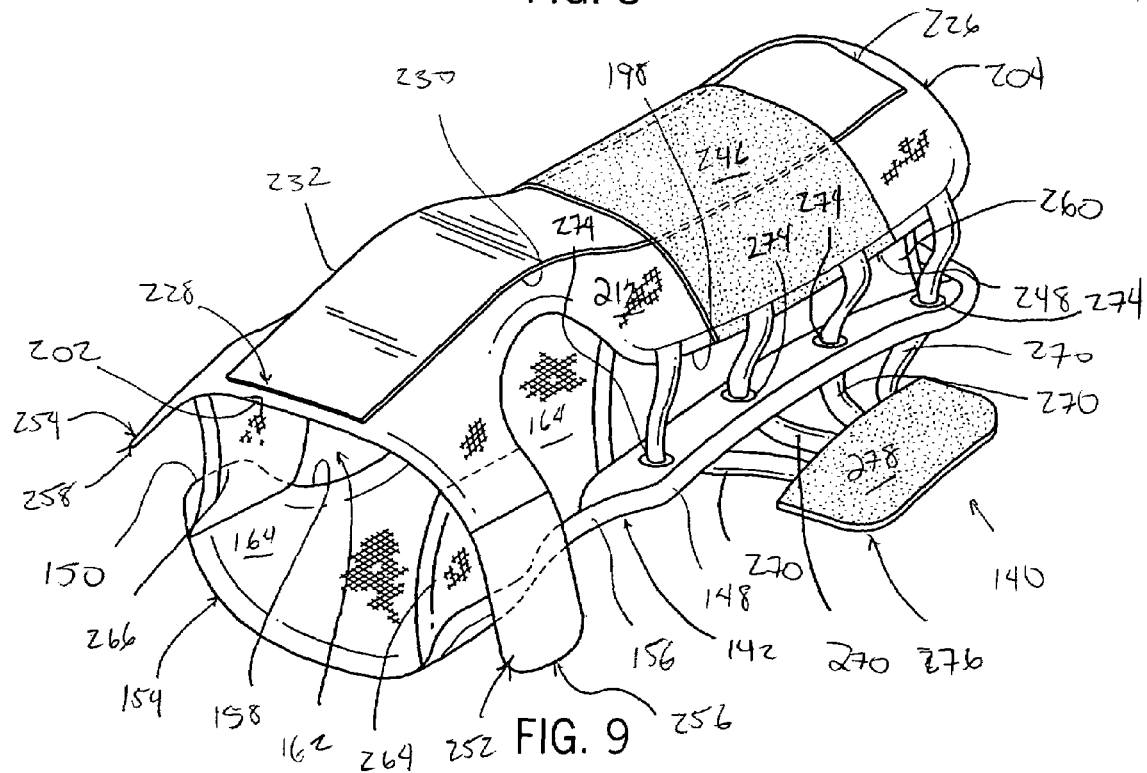
FIG. 9 is an isometric view of a second side of the wrist brace of FIG. 6.

First panel 26 further includes a first set of axially spaced, reinforced eyelets 60 extending therethrough adjacent first side 22 of first panel 12 and rearwardly of concave thumb receiving portion 23. In addition, first panel 26 includes a second set of axially spaced, reinforced eyelets 62 extending therethrough adjacent second side 24 of first panel 26 and rearwardly of concave thumb receiving portion 25 thereof. As best seen in FIGS. 2–3, eyelets 60 are adapted for receiving corresponding straps 64 therethrough and eyelets 62 are adapted for receiving corresponding straps 66 therethrough.

Second panel 14 is defined by first and second sides 68 and 70, respectively, and forward and rearward ends 72 and 74, respectively. First and second sides 68 and 70, respectively, include generally concave, thumb receiving portions 73 and 75, respectively. As best seen in FIG. 1, thumb receiving portion 23 of first side 22 of first panel 12 and thumb receiving portion 73 of first side 68 of second panel 14 define thumb aperture 27 in wrist brace 10. Similarly, thumb receiving portion 25 of second side 24 of first panel 12 and thumb receiving portion 75 of second side 70 of second panel 14 define thumb aperture 29 in wrist brace 10, FIG. 2.

Second panel 14 further includes inner surface 76 and outer surface 78. By way of example, second panel 14 may be formed of inner and outer sheets of materials 80 and 82, respectively, having absorbent layer 84 captured therebetween. Support 86 extends along a longitudinal axis and has inner surface 88 affixed to outer surface 78 of second panel 14 and an outer surface 90. Support 86 includes rearward end 92 positioned adjacent rearward end 74 of second panel 14 and forward end 93 adjacent forward end 72 of second panel 14. Support 86 further includes first and second sides 94 and 96 spaced from corresponding sides 68 and 70, respectively, of second panel 14. Support 86 further includes a concave portion 98 adjacent forward end 93 of second panel that extends away from first panel 12 and defines an enlarged portion of cavity 16 within wrist brace 10 for receiving the base of hand 18 of the wearer.

Cloth layer 100 overlaps support 86 and is interconnected to outer surface 78 of second panel 14 to secure support 86 in position. Pile pad 102 has a first end 104 adjacent first side 68 of second panel 14 and a second end adjacent second side 70 of second panel 14. Pile pad overlaps cloth layer 100 and is mounted to outer surface 78 of second panel 14 adjacent rearward end 74 thereof.

Second panel 14 further includes first and second connection tabs 106 and 108, respectively, extending laterally from forward end 72 thereof. Connection tabs 106 and 108 have generally arcuate terminal ends 110 and 112, respectively. Hooked pads are mounted to the inner surfaces of connection tabs 106 and 108 adjacent corresponding terminal ends 110 and 112, respectively, that are adapted to form a releasable connection with pile pad 56 mounted to outer surface 58 of cloth layer 54 adjacent forward end 26 of first panel 12. Connection tabs 106 and 108 allow a user to vary the size of opening 114 in the forward end of wrist brace 10 between forward end 26 of first panel 12 and forward end 72 of second panel 14 so as to snuggly retain wrist brace 10 about fingers 116 of hand 18 of the wearer. Terminal ends 110 and 112 of connection tabs 106 and 108, respectively, may be formed from a resilient material such as leather or the like so as to allow a user to repeatedly reposition the hooked pads on pile pad 56 as desired by the wearer.

First and second panels 12 and 14, respectively, are further connected by first and second rear webs 118 and 120, respectively. First rear web 118 extends between inner surface 30 of first panel 12 adjacent first side 22 thereof and inner surface 76 of second panel 14 adjacent first side 68 thereof. Similarly, second rear web 120 extends between inner surface 30 of first panel 12 adjacent second side 24 thereof and inner surface 76 of second panel 14 adjacent second side 70 thereof. It can be appreciated that first and second rear webs 118 and 120, respectively, are disposed rearwardly of corresponding thumb apertures 27 and 29, respectively, and are formed from a stretchable and breathable material.

Wrist brace 10 further includes first and second forward webs 122 and 124, respectively, for interconnecting first and second panels 12 and 14, respectively. First forward web 122 extends between inner surface 30 of first panel 12 adjacent first side 22 thereof and inner surface 76 of second panel 14 adjacent first connection tab 106. Second forward web 124 extends between inner surface 30 of first panel 12 adjacent second side 24 thereof and inner surface 76 of second panel 14 adjacent second connection tab 108. First and second forward webs 122 and 124, respectively, are disposed forwardly of corresponding thumb apertures 27 and 29, respectively, and are formed from a stretchable and breathable material.

In order to adjust the dimensions of cavity 16 through wrist brace 10 adjacent the rearward end thereof, first and second sets of straps 64 and 66, respectively, are provided. Straps 64 have first ends interconnected to and axially spaced along first side 68 of second panel 14 rearwardly of thumb aperture 27. Second ends of strap 64 are interconnected to a resilient connector generally designated by reference numeral 126. Connector 126 is formed from a resilient material and has a hooked pad affixed to the inner surface thereof. The hooked pad is adapted for forming a mating relationship with pile pad 102 affixed to outer surface 78 of second panel 14. Similarly, straps 66 have first ends interconnected to second panel 14 adjacent to and axially spaced along second side 70 of second panel 14. Second ends of straps 66 are interconnected to a connector generally designated by the reference numeral 128. Connector 128 includes an inner layer 130 in the form of a hooked pad adapted for releasably connecting with pile pad 102 and an outer pile pad 132. Pile pad 132 of connector 128 is adapted for receiving the hooked pad on the inner surface of connector 126, for reasons hereinafter described.

In operation, wrist brace 10 is slid over hand 18 and wrist 20 of a wearer such that fingers 116 of hand 18 project through opening 114 in the forward end of wrist brace 10 and such that the base of hand 18 is seated in the enlarged portion of cavity 16 in wrist brace 10 defined by concave portion 98 of support 86. If wrist brace 10 is intended to be worn on the right hand of a wearer, thumb 140 of hand 18 is inserted through thumb aperture 29 in wrist brace 10. In the event that wrist brace 10 is intended to be worn on the left hand of a wearer, thumb 140 is inserted through thumb aperture 27 in wrist brace 10.

In order to snuggly retain wrist brace 10 on hand 18 and wrist 20 of a wearer, connection tabs 106 and 108 adjacent forward end 72 of second panel 14 are wrapped around the forward end 26 of first panel 12 and connected to pile pad 56 utilizing the hooked pads along the inner surfaces thereof. It can be appreciated that the location of the terminal ends 110 and 112 of connection tabs 106 and 108, respectively, may be varied such that the forward end of wrist brace 10 is snuggly wrapped around fingers 116 of the wearer.

In order to snuggly retain wrist brace 10 on wrist 20 of the wearer, connector 128 is pulled such that straps 66 are taut. Thereafter, hooked pad 130 of connector 128 is connected to pile pad 102 along outer surface 78 of second panel 14. It can be appreciated that as straps 66 are pulled taut, second side 24 of first panel 12 is brought toward second side 70 of second panel 14 by straps 66 passing through eyelets 62. Thereafter, connector 126 is used to bring straps 64 taut around wrist 20 of the wearer. With straps 64 taut, the hooked pad of connector 56 is connected to pile pad 102 along outer surface 78 of second panel 14. Alternatively, in the event that a wearer's wrist is small, the hooked pad of connector 126 may be connected to pile pad 132 along the outer surface of connector 128, FIG. 5. As described, wrist brace 10 is snuggly retained on hand 18 and wrist 20 of the wearer so as to restrict movement of wrist 20 that may generate discomfort for the wearer.

Referring to FIGS. 6–10, a second embodiment of a wrist brace in accordance with the present invention is shown designated by the reference numeral 140. Wrist brace 140 includes first and second panels 142 and 144, respectively, that define cavity 146 therebetween for receiving a portion of hand 18 and wrist 20 of a wearer. As hereinafter described, wrist brace 140 is adaptable to be worn on either the left or the right wrist of a wearer.

First and second panels 142 and 144, respectively, extend along corresponding axes and formed from a stretchable and breathable material that allows liquid, such as perspiration, to be drawn away from contact with the skin of the wearer. First panel 142 is defined by first and second sides 148 and 150, respectively, and forward and rearward ends 152 and 154, respectively. First and second sides 148 and 150 include thumb receiving portions 156 and 158 that partially define thumb apertures 160 and 162, respectively, and wrist brace 140, as hereinafter described. First panel 142 further includes inner surface 164 and outer surface 166. By way of example, first panel 142 may be formed of inner and outer sheets of material 168 and 170, respectively, having absorbent layer 172 captured therebetween.

Wrist brace 140 further includes a generally flat rigid support 174 having inner surface, 176 abutting outer surface 170 of first panel 142 and an outer surface 178. Support 174 includes a rearward end 180 adjacent rearward end 154 of first panel 142 and forward end 182 adjacent forward end 154 of first panel 142. The sides of support 174 are generally parallel to each other and spaced from corresponding sides 148 and 150 of first panel 142. Cloth layer 184 overlaps support 174 and is interconnected to outer surface 170 of first panel 142 to secure support 174 in position. Pile pad 186 overlaps cloth layer 54 and extends from rearward end 152 of first panel 142 to forward end 154 of first panel 142. Pile pad 186 is adapted to receive a hooked pad 188 mounted to outer surface 190 of pillow 192. Pillow 192 is defined by rearward end 194 and forward end 196 and is of a length generally equal to the length of wrist brace 140, FIG. 8. Hooked pad 188 is adapted for releasably interconnecting pillow 192 to pile pad 186 of wrist brace 140, FIG. 6. It is intended that pillow 192 be resilient and protect wrist 20 from impact.

Second panel 144 is defined by first and second sides 198 and 200, respectively, and forward and rearward ends 202 and 204, respectively. First and second sides 198 and 200, respectively, of second panel 144 include generally concave thumb receiving portions 206 and 208, respectively. Thumb receiving portion 156 of first side 148 of first panel 142 and thumb receiving portion 206 of first side 198 of second panel 142 define thumb aperture 160 in wrist brace 140. Similarly, thumb receiving portion 158 of second side 150 of first panel 142 and thumb receiving portion 208 of second side 200 of second panel 144 define thumb aperture 162 in wrist brace 140, FIG. 9.

Second panel 144 of wrist brace 140 further includes inner surface 210 and outer surface 212. By way of example, second panel 144 may be formed of inner and outer sheets of material 214 and 216, respectively, having absorbent layer 218 captured therebetween. Support 220 extends along a longitudinal axis and has inner surface 222 affixed to outer surface 212 of second panel 144 and an outer surface 224. Support 220 includes rearward end 226 positioned adjacent rearward 204 of second panel 144 and forward end 228 adjacent forward end 202 of second panel 144. Support 220 further includes first and second sides 230 and 232 spaced from corresponding sides 198 and 200 of second panel 144. Support 220 defines a concave portion 236 adjacent forward end 202 of second panel 144 that extends away from first panel 142. Concave portion 236 of support 220 defines an enlarged portion of cavity 146 for receiving pillow 238. Pillow 238 includes an outer shell 240 for housing resilient material 242. Pillow 238 is affixed to inner surface 210 of second panel 144 adjacent forward end 202 thereof. It is intended that pillow 238 engage the base of hand 18 of the wearer, as hereinafter described.

Cloth layer 244 overlaps support 220 and is interconnected to outer surface 212 of second panel 144 to secure support 220 in position. Pile pad 246 has a first end 248 adjacent first side 198 of second panel 144 and a second end 250 adjacent second side 200 of second panel 144. Pile pad 246 overlaps cloth layer 244 and is mounted to outer surface 212 of second panel 144 adjacent rearward end 204 thereof.

Second panel 144 further includes first and second connection tabs 252 and 254, respectively, extending laterally from forward end 202 thereof. Connection tabs 252 and 254 have generally arcuate terminal ends 256 and 258, respectively. Hooked pads are mounted to the inner surfaces of connection tabs 252 and 254 adjacent corresponding terminal ends 256 and 258, respectively, and are adapted to form releasable connections with pile pad 186 mounted to the cloth layer 178 that overlaps support 174. Connection tabs 252 and 254 allow a user to vary the size of opening 259 in the forward end of wrist brace 140 between forward end 154 of first panel 142 and forward end 202 of second panel 144 so as to snuggly retain wrist brace 140 about fingers 116 of hand 18 of a wearer. Terminal ends 256 and 258 of connection tabs 252 and 254, respectively, may be formed from a resilient material such as leather or the like to allow the user to repeatedly reposition the hook pads along the inner surfaces of connection tabs 252 and 254 on pile pad 186 as desired by the wearer.

First and second panels 142 and 144, respectively, of wrist brace 140 are further connected by first and second rear webs 260 and 262, respectively. First rear web 260 extends between inner surface 164 of first panel 142 adjacent first side 148 thereof and inner surface 210 of second panel 144 adjacent first side 198 thereof. Similarly, second rear web 262 extends between inner surface 164 of first panel 142 adjacent the second side 150 thereof and inner surface 210 of second panel 144 adjacent side 150 thereof. It can be appreciated that first and second rear webs 260 and 262, respectively, are disposed rearwardly of corresponding thumb apertures 160 and 162, respectively, and are formed from a stretchable and breathable material.

Wrist brace 144 further includes first and second forward webs 264 and 266, respectively, for interconnecting first and second panels 142 and 144, respectively. First forward web 264 extends between inner surface 164 of first panel 142 adjacent first side 148 thereof and inner surface 210 of second panel 144 adjacent first connection tab 252. Second forward web 266 extends between inner surface 164 of first panel 142 adjacent second side 150 thereof and inner surface 210 of second panel 144 adjacent second connection tab 254. First and second forward webs 264 and 266, respectively, are disposed forwardly of corresponding thumb apertures 160 and 162, respectively, and are formed from a stretchable and breathable material.

In order to adjust the dimensions of cavity 146 in wrist brace 140 adjacent the rearward end thereof, first and second sets of straps 270 and 272, respectively are provided. Straps 270 have first ends interconnected to an axially spaced along first side 198 of second panel 144 rearwardly of thumb aperture 160 and extend through corresponding eyelets 274 extending through and spaced along first side 148 of first panel 142. Second ends of straps 270 are interconnected to a resilient connector generally designated by the reference numeral 276. Connector 276 is formed from a resilient material and has hooked pad 278 affixed to the inner surface thereof. Hooked pad 278 is adapted for forming a mating relationship with pile pad 246 affixed to outer surface 212 of second panel 144. Similarly, straps 272 have first ends interconnected to second panel 144 adjacent to and axially spaced along second side 200 thereof and extend through corresponding eyelets through second side 150 of first panel 142. Second ends of straps 272 are interconnected to a connector generally designated by the reference number 280. Connector 280 includes hooked pad 282 along the inner surface thereof for releasably connecting connector 280 with pile pad 246 and pile pad 284 along the outer surface thereof. Pile pad 284 is adapted for receiving hooked pad 278 of connector 276, for reasons hereinafter described.

In operation, wrist brace 140 slid over hand 18 and wrist 20 of the wearer such that fingers 116 of hand 18 projects through opening 259 and the forward end of wrist brace 140 and such that the base of hand 18 is seated against pillow 238 within cavity 146. If wrist brace 140 is intended to be worn on the right hand of a wearer, thumb 140 of hand 18 is inserted through thumb aperture 162 in wrist brace 140. In the event that wrist brace 140 is intended to be worn on the left hand of a wearer, thumb 140 is inserted into thumb aperture 160 in wrist brace 140.

In order to snuggly retain the forward end of wrist brace 140 on hand 18 of a wearer, connection tabs 252 and 254 adjacent forward end 202 of second panel 144 are wrapped around the forward end 154 of first panel 142 and connected to pile pad 186 utilizing the hooked pad along the inner surfaces thereof. It can be appreciated that the location of the terminal ends 256 and 258 of connection tabs 252 and 254, respectively, may be varied such that the forward end of wrist brace 140 is snuggly wrapped around fingers 116 of the wearer. In order to snuggly retain the rearward end of wrist brace 140 on wrist 20 of the wearer, connector 280 is pulled such that straps 272 are taut. Thereafter, hooked pad 282 of connector 280 is connected to pile pad 246 along outer surface 212 of second panel 144. It can be appreciated that the straps 272 are pulled taut, second side 150 of first panel 142 is brought towards second side 200 of second panel 144 by straps 272 passing through the eyelets through first panel 142 adjacent second side 150 thereof. Thereafter, connector 276 is used to bring straps 270 taut around wrist 20 of the wearer. With straps 270 taut, hooked pad 278 along inner surface of connector 276 is connected to pile pad 246 along outer surface 212 of second panel 144. Alternatively, in the event that a wearer's wrist is small, hooked pad 278 along the inner surface of connector 276 may be connected to pile pad 284 along the outer surface of connector 280.

As described, wrist brace 140 is snuggly retained on hand 18 and wrist 20 of the wearer so as to restrict movement of wrist 20 that may generate discomfort to the wearer. In addition, in order to prevent damage to wrist 20 associated with the inadvertent impact of wrist 20, pillow 192 may be affixed to pile pad 186 along first panel 142.

Various modes of carrying out the invention are contemplated as being within the scope of the following claims particularly pointing out and distinctly claiming the subject matter that is regarded as the invention.

We claim:

1. A wrist brace for supporting a wrist and a hand of an individual, the hand including a first side and a second opposite palm side, comprising:
   a first panel having inner and outer surfaces, a forward end, a rearward end and first and second sides, the inner surface of the first panel positionable on the first side of the hand;
   a second panel having inner and outer surfaces, a forward end, a rearward end and first and second sides, the inner surface of the second panel and the inner surface of the first panel defining a cavity for receiving the wrist of the individual;
   a first generally flat rigid support disposed in the first panel and extending between the forward and rearward ends thereof;
   a second rigid support disposed in the second panel and extending between the forward and rearward ends thereof, the second rigid support having a concave portion extending away from the first panel;
   a pillow removably connectable to the outer surface of the first panel;
   a hook and pile fastener for interconnecting the pillow to the outer surface of the first panel; and
   a second pillow extending from the inner surface of the second panel adjacent to the forward end of the second panel.

2. A wrist brace for supporting a hand and wrist of a wearer the hand having a first side and a second, opposite side including a palm, comprising:
   first and second rigid support members defining a cavity therebetween for receiving at least a portion of the hand and wrist of the wearer, the first rigid support member positionable on the first side of the hand and the second rigid support member positionable on the second side of the hand;
   a removable pillow operatively connectable to the first rigid support member;
   a hook and pile fastener for interconnecting the pillow to the outer surface of the first panel; and
   a second pillow operatively connected to the second panel and extending into the cavity.

3. A wrist brace for supporting a hand and wrist of a wearer, comprising:
- a first flexible panel having an inner surface, an outer surface, a forward end, a rearward end, and first and second sides;
- a generally flat, first support disposed in the first flexible panel, the first support discouraging flexing of the first flexible panel;
- a second flexible panel having an inner surface, an outer surface, a forward end, a rearward end, and first and second sides;
- a second support disposed in the second flexible panel, the second support having a concave portion defining a recess for receiving a portion of the hand of the wearer;
- a first rear web interconnecting the first side of the first panel and the first side of the second panel;
- a first forward web for interconnecting the first side of the first panel and the first side of the second panel, the first rear web and the first forward web are axially spaced so as to define a thumb aperture therebetween;
- a second rear web for interconnecting the second side of the first panel and the second side of the second panel;
- a second forward web for interconnecting the second side of the first panel and the second side of the second panel, the second rear web and the second forward web being axially spaced so as to define a second thumb aperture therebetween; and
- a connector for adjustably interconnecting the first side of the first panel and the first side of the second panel to vary the size of the cavity.

4. The wrist brace of claim 3 wherein the first panel includes an eyelet extending therethough adjacent the first side and wherein the connector extends through the eyelet and includes a first end interconnected to the first side of the second panel and a second end having a fastener connectable to the outer surface of the second panel.

5. The wrist brace of claim 4 further comprising a hook and pile fastener having a hooked portion and a pile portion, wherein one of the hooked portion and the pile portion is interconnected to the outer surface of the second panel and wherein the fastener includes the other of the hooked portion and the pile portion.

6. The wrist brace of claim 3 further comprising a pillow and a hook and pile fastener for removably interconnecting the pillow to the outer surface of the first panel.

7. The wrist brace of claim 3 further comprising a second pillow operatively connected to the second panel and extending into the cavity.

8. The wrist brace of claim 3 further comprising first and second connection tabs extending from the second panel; and a connection structure for removably connecting the first and second connection tabs to the first panel.

9. A wrist brace for supporting a wrist of an individual, comprising:
- a first panel having inner and outer surfaces, a forward end, a rearward end and first and second sides;
- a second panel having inner and outer surfaces, a forward end, a rearward end and first and second sides, the inner surface of the second panel and the inner surface of the first panel defining a cavity for receiving the wrist of the individual;
- a first generally flat rigid support disposed in the first panel and extending between the forward and rearward ends thereof;
- a second rigid support disposed in the second panel and extending between the forward and rearward ends thereof the second rigid support having a concave portion extending away from the first panel;
- a first rear web interconnecting the first side of the first panel and the first side of the second panel;
- a first forward web for interconnecting the first side of the first panel and the first side of the second panel, the first rear web and the first forward web are axially spaced so as to define a thumb aperture therebetween;
- a second rear web for interconnecting the second side of the first panel and the second side of the second panel; and
- a second forward web for interconnecting the second side of the first panel and the second side of the second panel;

wherein the second rear web and the second forward web are axially spaced so as to define a second thumb aperture therebetween.

10. A wrist brace for supporting a hand and wrist of a wearer, comprising:
- first and second rigid support members defining a cavity therebetween for receiving at least a portion of the hand and wrist of a wearer,
- the first rigid support member including:
  - a first flexible panel having an inner surface, an outer surface, a forward end, a rearward end, and first and second sides; and
  - a generally flat, first support disposed in the first flexible panel, the first support discouraging flexing of the first flexible pad;
- the second rigid support member including:
  - a second flexible panel having an inner surface, an outer surface, a forward end, a rearward end, and first and second sides; and
  - a second support disposed in the second flexible panel, the second support having a concave portion defining a recess for receiving a portion of the hand of the wearer;
- a first rear web interconnecting the first side of the first panel and the first side of the second panel;
- a first forward web for interconnecting the first side of the first panel and the first side of the second panel, the first rear web and the first forward web are axially spaced so as to define a thumb aperture therebetween;
- a second rear web for interconnecting the second side of the first panel and the second side of the second panel;
- a second forward web for interconnecting the second side of the first panel and the second side of the second panel; and
- a removable pillow operatively connectable to the first rigid support member;

wherein the second rear web and the second forward web are axially spaced so as to define a second thumb aperture therebetween.

* * * * *